United States Patent [19]

Hesselink

[11] 4,171,915
[45] Oct. 23, 1979

[54] LASER INTERFEROMETER PROBE

[75] Inventor: Lambertus Hesselink, Pasadena, Calif.

[73] Assignee: The United States of America as represented by the Secretary of the Air Force, Washington, D.C.

[21] Appl. No.: 840,331

[22] Filed: Oct. 7, 1977

[51] Int. Cl.² ............................................. G01B 9/02
[52] U.S. Cl. ................................................ 356/361
[58] Field of Search .................. 356/106 R, 107, 113, 356/361

[56] References Cited

U.S. PATENT DOCUMENTS

| | | | |
|---|---|---|---|
| 2,795,991 | 6/1957 | Tuzi | 356/107 |
| 3,819,278 | 6/1974 | Muller | 250/227 |

*Primary Examiner*—Conrad J. Clark
*Attorney, Agent, or Firm*—Joseph E. Rusz; Willard R. Matthews, Jr.

[57] ABSTRACT

Index of refraction measurements are made by means of an optical device in which a coherent light beam is divided into an object beam and a reference beam, each of which is directed through a separate path in a common light transmitting medium. The object beam is also transmitted en route through a test volume that accommodates a substance to be tested. It is subsequently recombined with the reference beam to form a single output beam. The output beam is received by a photo detector and its intensity is measured. The intensity of the detected output beam is related to any phase shift between the object and reference beams. The phase shift in turn is a measure of the index of refraction of the test substance. Information relating to density, temperature and pressure of the test substance can be derived from measured index of refraction values by using conventional conversion formulas. An operating range control is provided by introducing a volume of pressurized gas into the paths of the object and reference beams. The operating range of the instrument is set by adjusting the pressure of the gas in the absence of a test substance.

4 Claims, 6 Drawing Figures

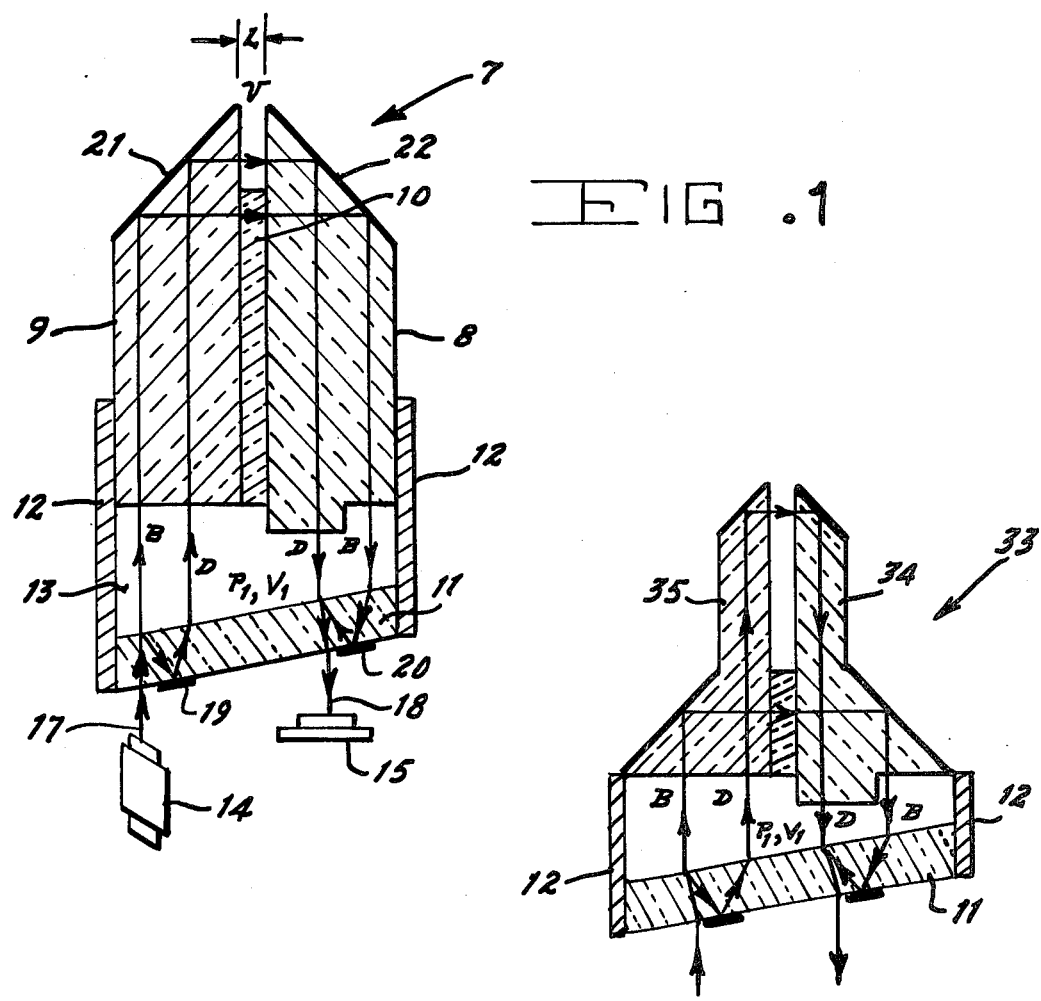
FIG. 1
FIG. 5
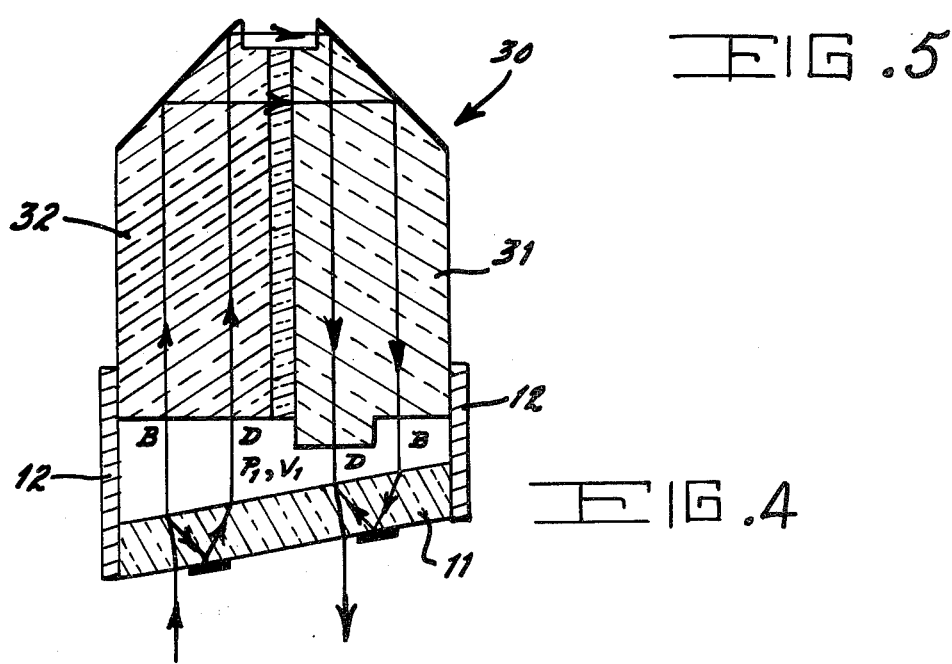
FIG. 4

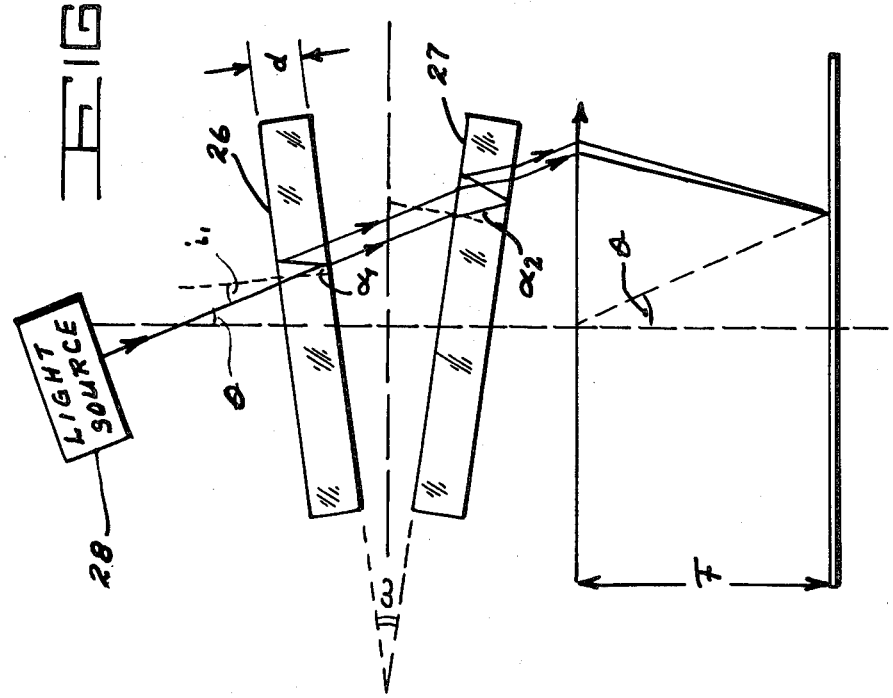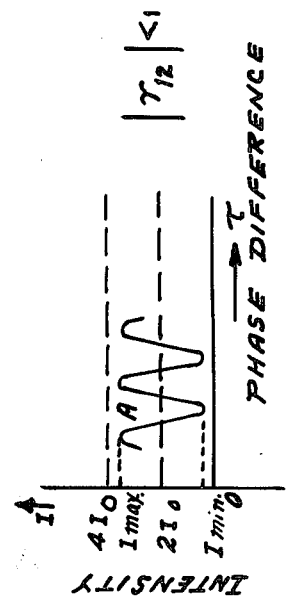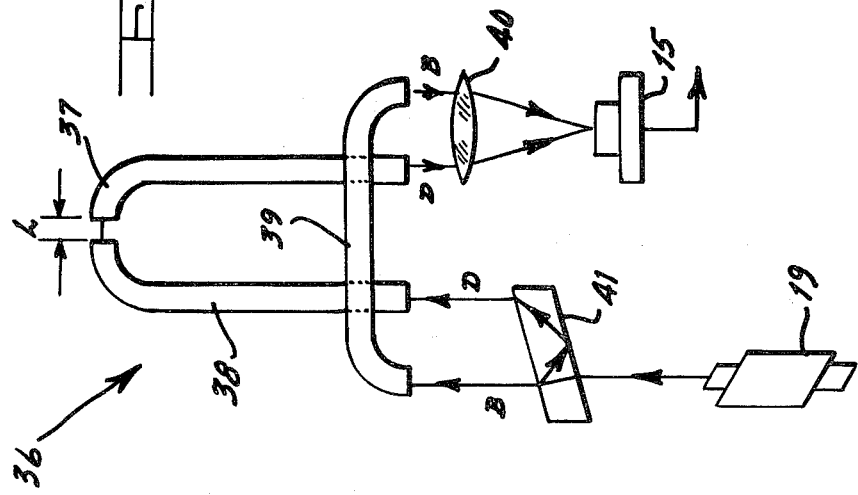

LASER INTERFEROMETER PROBE

STATEMENT OF GOVERNMENT INTEREST

The invention described herein may be manufactured and used by or for the Government for governmental purposes without the payment of any royalty thereon.

BACKGROUND OF THE INVENTION

This invention relates to laser interferometer probes, and in particular, to interferometers of the type used to determine the properties of gases and other test substances.

There are many industrial and laboratory processes in which local measurements of test substances must be made rapidly and with a high degree of accuracy. For this purpose various interferometer and other type probes have been used. These state-of-the-art devices have limitations that often reduce their effectiveness, however. The large size of such devices often results in interference with the flow of fluids being tested; spatial and frequency response characteristics could be improved upon; and the accuracy of most conventional probes is inadequate for many applications. Furthermore, different probes are usually required for different type measurements. Accordingly, there currently exists the need for a multipurpose, miniturized probe that is extremely accurate and that has improved spatial and frequency response characteristics. The present invention is directed toward satisfying that need.

SUMMARY OF THE INVENTION

The laser interferometer probe of the invention comprises a probe structure, a coherent light beam source, a beam splitter plate and a photo detector. The beam splitter plate divides the beam from the coherent light beam source into an object beam and a reference beam. The probe structure consists of two juxtaposed transluscent prisms that, in combination, are configured to define a volume for the accommodation of test substances. The coherent light beam source and beam splitter plate are arranged to direct the object and reference beams into the probe structure. Mirrored portions of the transluscent prisms cause the object and reference beams to follow parallel paths through the probe structure with the object beam also passing through the test volume. The two beams emerge from the probe structure to terminate on the beam splitter plate whereby they are recombined to form an output beam. The output beam is detected and its intensity measured by the photodetector. The beam splitter plate is spaced from and connected to the probe structure by a metal shrowd. This provides a hermetically sealed region of pressurized gas wherethrough the object and reference beams pass. Instrument operating range control is provided by adjusting the gas pressure in the absence of a test substance. In an alternative embodiment of the invention the object and reference beam paths are directed through fiber optics elements.

It is a principal object of the invention to provide a new and improved laser interferometer probe.

It is another object of the invention to provide a laser interferometer probe that is smaller and has a higher degree of accuracy than currently available devices.

It is another object of the invention to provide a laser interferometer probe having improved spatial and frequency response characteristics.

It is another object of the invention to provide a laser interferometer probe capable of detecting information relating to the density temperature and pressure of test substances.

It is another object of the invention to provide a laser interferometer probe that utilizes fiber optics elements.

It is another object of the invention to provide a laser interferometer probe having means for setting the desired operating range.

These, together with other objects, features, and advantages of the invention will become more readily apparent from the following detailed description taken together with the illustrative embodiments in the accompanying drawings.

DESCRIPTION OF THE DRAWINGS

FIG. 1 is a schematic illustration of one embodiment of the probe of the invention utilizing a translucent prism type probe structure;

FIG. 2 illustrates light beam paths through a divided beam splitter plate and lens;

FIG. 3 is a waveform illustrating the recombined beam of FIG. 2;

FIGS. 4 and 5 illustrate alternative configurations of the embodiment of the probe shown in FIG. 1; and FIG. 6 illustrates a probe of the type comprehended by the invention utilizing fiber optics elements.

DETAILED DESCRIPTION OF THE PREFERRED EMBODIMENTS

An interferometer measures index of refraction changes. For gases this index of refraction is related to the density by the Gladstone-Dale law; for liquids, such as water, this index is related to the temperature. For shock waves in gases the density is uniquely related to the pressures which determines the Mach number of the wave. So, by measuring index of refraction changes, information regarding density, temperature, or pressure of a medium may be obtained. The present invention is a probe that is capable of making such index of refraction measurements. It is based on the interferometer principle and has high frequency and spatial resolution characteristics. The probe is axisymmetric or rectangular in cross section and one presently preferred embodiment thereof is illustrated schematically by the prism type probe 7 of FIG. 1. Probe 7 comprises transluscent (glass) prisms 8 and 9 separated by glass member 10. In the arrangement of FIG. 1 these elements cooperate to define a test volume V. A beam splitter plate 11 is connected to the prisms by means of a metal shrowd 12. These elements enclose a hermetically sealed region 13 wherein pressurized gas may be inserted to provide device operating range controls. A coherent light beam 17 is generated by laser source 14. Beam 17 is divided into a reference beam B and an object beam D by the beam splitter plate 11. These beams are directed through the device and the beam splitter plate by the geometry of the prisms and the beam splitter plate, and by mirrored surfaces 19, 20, 21 and 22. The recombined output beam 18 is detected by photodetector 15.

In operation, the incident polarized laser beam 17 is divided into two beams, B (bright) and D (dim), by the beam splitter plate 11. The intensities of the two emerging beams are determined by the thickness of the beam splitter and the angle of incidence and may be calculated from Fresnel's formulae. The two beams, B and D, enter prism 9 and are reflected over a 90° angle at the top of the prism. The object beam, D, passes through a measuring volume V, and the reference beam passes through the glass plate 10, sandwiched between prisms 8 and 9. The reference and object beams recombine on the same splitter plate 11 and the resulting emitted beam 18 goes to photo detector 15 which measures its intensity. In this embodiment the optical path difference between object beam and reference beam is zero.

The location of the fringes can be found most easily by analyzing FIG. 2. Splitter plate 11 is divided into two parts along its symmetry plane, and the probe is folded open to form optical flats 26, 27. The two optical flats are assumed to make an angle $\omega$ with each other, and the interferometer is illuminated with an extended monochromatic light source 28. On the film, fringes will form which are straight lines and parallel to the apex of the two optical flats. Since:

$$\Delta = 2nd \cos \alpha_1 - 2nd \cos \alpha_2 + \delta$$
$$= \frac{2\theta\omega d}{n} + \delta$$

The fringe separation is found to be $D \approx Fn\lambda/2\omega d$
where
F: focal length
n: index of refraction of the splitter plate glass
$\lambda$: wavelength of light in vacuum
$\omega$: angle between optical flats
d: thickness of optical flats The probe in FIG. 1 is designed for an infinite fringe width setup.

When the index of refraction in the sampling volume changes from n' to n, a phase change $$\delta = (2\pi/\lambda)L(n'-n)$$

between the object and reference beam results. L is the geometrical distance between prisms I and II. Consequently, the intensity of the recombined beams measured at the detector changes as a function of $\delta$.

$$I = 2I_o + 2I_o \cos(\alpha_{12}(\tau) + 2\pi\nu\tau) \cdot |\gamma_{12}(\tau)|$$

where
$\alpha_{12}$: argument $(\gamma_{12}(\tau)) - 2\pi\nu\tau$
$\gamma_{12}$: complex degree of coherence
$\nu$: mean frequency of the laser light
$I_o$: intensity beam D
$\tau = L(n'-n_o)/c_o$
Co=: speed of light in a vacuum.

The pressure inside hermetically sealed region 13 (volume $V_1$) can be varied so as to change the phase difference between object beam and reference beam in the absence of a test gas. In this fashion the intensity of the recombined beam 18 can be set at a working point A* (see FIG. 3). By making L small enough so as to keep $\delta$ less than $\pi$, the intensity on the detector will only vary between $I_{max}$ and $I_{min}$ for the same fringe. However, by keeping track of the number of maxima and minima that pass the detector, phase changes larger than $\pi$ can be allowed, and the index of refraction change can be deduced unambiguously from the measured intensity change.

For a mixture of two gases the concentration is related to the index of refraction in the following fashion:

$$n' = \alpha n_1 + (1-\alpha)n_2,$$

$$\rho_{mix} = \alpha\rho_1 + (1-\alpha)\rho_2$$

where
$n_{1,2}$: index of refraction gas 1,2
$\rho_{1,2}$: density of gas 1,2
$\alpha$: partial pressure gas 1.

By way of example an in order to give an impression of the minimal obtainable size of the instrument, the geometry for a probe that is designed to measure the concentration of helium in carbon dioxide at atmospheric pressure is here calculated. For a maximum phase change $\pi/4$, the length L of the measuring volume is L=0.18 mm($\lambda$=6000 A). The diameter of the laser beam over this length can be reduced to 0.22 mm (with a depth of field of 65 mm). The amplitude resolution of the intensity is determined by the input power of the laser beam going into the instrument and by the noise characteristics of the detector. With a 1 mW He-Ne laser, a resolution of 1 A in optical path length, i.e., (n'−n)L per 1 $\mu$sec, may be obtained. The rectangular cross section of the probe can be made as small as 1 mm×4 mm.

Depending upon the application, alternative configurations may be used to obtain the most optimal working conditions. For instance, the prism type probe 30 of FIG. 4 utilizes prisms 31, 32 whose geometric configuration permits L to be made large, but the optical path difference small. Spatial resolution is sacrificed however. The prism type probe 33 of FIG. 5 on the other hand has prisms 34,35 whose geometry minimizes the disturbance to the flow near the measuring region. Fiberoptics elements can also be used in the practice of the invention. Using the approach spatial resolution can be improved and the size of the probe reduced. FIG. 6 illustrates a fiber optics type probe 36 that utilizes fiber optics elements 37,38,39 to direct the object of reference beams. The input beam is split by beam splitter 41 and the output beams are combined by a lens 40 or another beam splitter plate.

While the invention has been described in terms of its presently preferred embodiments, it is understood that the words which have been used are words of description rather than words of limitation and that changes within the purview of the appended claims may be made without departing from the scope and spirit of the invention in its broader aspects.

What is claimed is:

1. An inteferometer probe comprising means for generating a beam of coherent light,
   beam splitting means for dividing said beam of coherent light into an object beam and a reference beam,
   a probe structure in the form of a transluscent axisymmetric member having a prismatic end that in part defines a test volume for the accommodation of a test substance, and a beam input/output end,
   a beam splitter plate,
   light beam combining means for recombining said object and reference beams to form an output beam, said beam splitting means and said light beam combining means being integral portions of said beam splitter plate, said beam splitter plate being in spaced proximity to the beam input/output end of said transluscent axisymmetric member,
   a sleeve member encompassing said beam splitter plate and the outer end surface of said probe structure effecting a hermetically sealed volume therebetween, pressurized gas in said hermetically sealed volume, the pressure of said gas being a function of the operating range of the interferometer probe, means for directing said reference beam through said probe structure to terminate at said light beam combining means, means for directing said object beam through said probe structure and said test volume to terminate at said light beam combining means, and detector means for detecting and measuring the intensity of the combined output beam from said light beam combining means.

2. An interferometer probe as defined in claim 1 wherein said probe structure is configured to provide equal optical path lengths for said object and reference beams.

3. An interferometer probe as defined in claim 1 wherein said probe structure is configured to provide a longer optical path length for said object beam than for said reference beam.

4. An interferometer probe as defined in claim 1 wherein said beam splitter plate has a thickness and angle of incidence relative to said beam of coherent light that provides a high intensity reference beam and a low intensity object beam.

* * * * *